United States Patent [19]

Wyler

[11] Patent Number: 4,805,625
[45] Date of Patent: Feb. 21, 1989

[54] SPHENOIDAL ELECTRODE AND INSERTION METHOD

[75] Inventor: Allen R. Wyler, Memphis, Tenn.

[73] Assignee: Ad-Tech Medical Instrument Corporation, Racine, Wis.

[21] Appl. No.: 71,075

[22] Filed: Jul. 8, 1987

[51] Int. Cl.[4] .............................................. A61N 1/00
[52] U.S. Cl. .................................... 128/642; 128/639
[58] Field of Search ................. 128/784, 785, 642, 639

[56] References Cited

U.S. PATENT DOCUMENTS

| | | | |
|---|---|---|---|
| 4,408,610 | 10/1983 | Sarnoff | 128/642 |
| 4,616,656 | 10/1986 | Nicholson et al. | 128/630 |
| 4,630,617 | 12/1986 | Ritter et al. | 128/784 |

OTHER PUBLICATIONS

Cald Well et al., "A Percutaneous Wire Electrode for Chronic Research Use" IEEE Trans. on Bio. Med. Eng. vol. 22, No. 5, pp. 429–432, Sep. 1975.

Primary Examiner—Francis Jaworski
Assistant Examiner—George Manuel
Attorney, Agent, or Firm—Peter N. Jansson, Ltd.

[57] ABSTRACT

An improved apparatus and method for insertion of a sphenoidal wire electrode. The apparatus includes a needle (22) carrying a wire (24) having a turned-back distal portion (34) beside the needle and terminating forwardly along the slant-tip (28). The method includes positioning the wire in the needle with such turned-back distal portion as described, inserting the needle and wire, engaging the tissue with the turned-back portion to resist unintended relocation during needle withdrawal and the subsequent test period, and unfolding the turned-back portion of the wire to straighten it by initial pulling of the wire after the test period.

6 Claims, 1 Drawing Sheet

U.S. Patent  Feb. 21, 1989  4,805,625
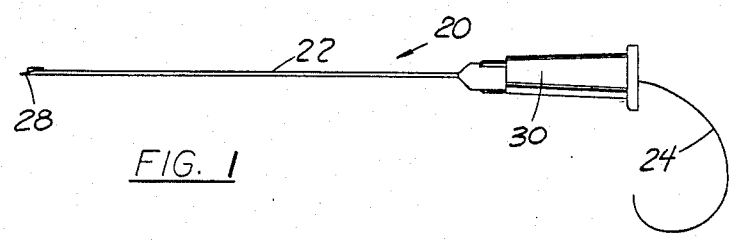
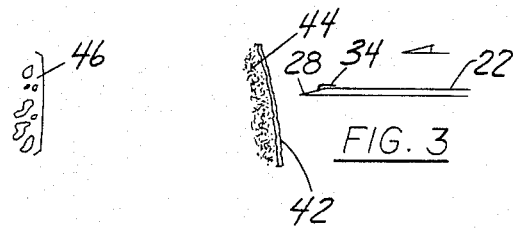
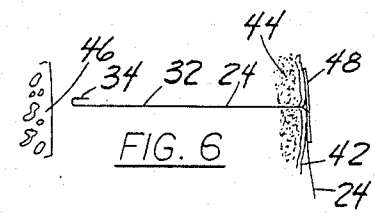
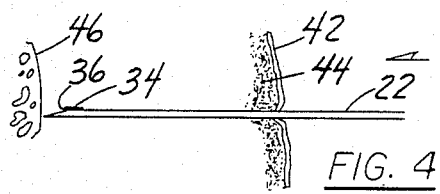
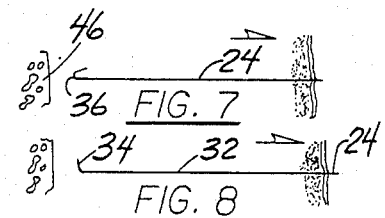
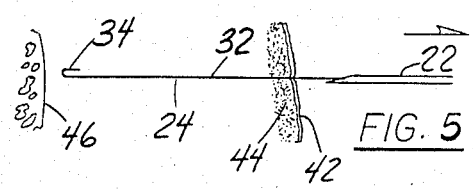
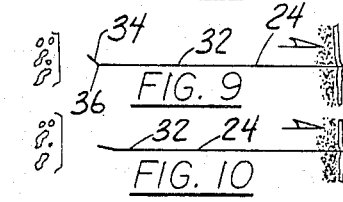
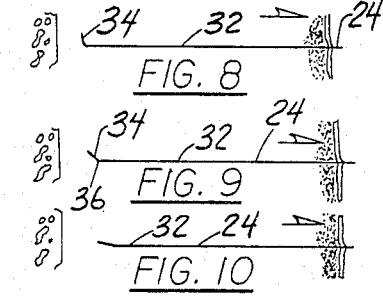
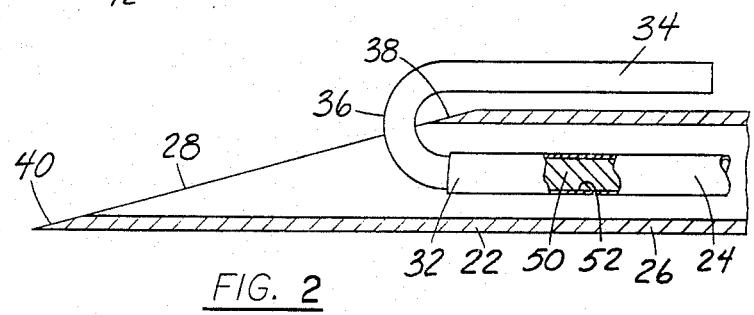

SPHENOIDAL ELECTRODE AND INSERTION METHOD

FIELD OF THE INVENTION

This invention is related generally to electrodes and insertion of electrodes used for detection of epileptiform discharges and, more particularly, to apparatus and methods for manipulation of sphenoidal wire electrodes for such purposes.

BACKGROUND OF THE INVENTION

Sphenoidal electrodes, which were introduced in the late 1940s and early 1950s, are reported to be superior to nasopharyngeal electrodes and ear electrodes for detecting mesial temporal lobe epileptiform discharges. See "Mesial Temporal Spikes: A Simultaneous Comparison of Sphenoidal, Nasopharyngeal, and Ear Electrodes," by Sperling et al., in *Epilepsia*, Vol. 27, No. 1 (1986).

A sphenoidal electrode is a wire which is inserted by a physician into the jaw muscle and nearby tissue to a position near the sphenoid bone where it remains during a test period to sense epileptiform discharges. More specifically, the site of insertion is approximately 3-4 mm below the zygoma and 2-3 cm in front of the tragus.

In one insertion technique, the sphenoidal wire electrode is inserted by means of a hollow needle which contains a straight section of such wire terminating in a straight distal end. During insertion, the needle and wire are advanced medially until the tip of the needle strikes bone. The needle is then withdrawn along the wire leaving the wire inserted for the duration of the test period. During the test period, which may extend for as long as five days or more, the opposite end of the sphenoidal electrode wire is electrically connected to an EEG jack box, usually via another wire. After the test period, the wire electrode is removed by pulling it out.

While sphenoidal wire electrodes are preferred for detecting mesial temporal lobe epileptiform discharges, significant problems have been experienced in proper insertion of such electrodes. Inserting the electrode wire such that its distal end reliably arrives and stays at the intended location for optimal discharge detection may be difficult for various reasons.

There is a tendency during insertion of the needle and contained wire for the wire to be pushed along the needle, farther into the needle, away from the needle tip. This may be caused by tissue which impacts the wire during the insertion motion.

Improper location of the distal end of the sphenoidal electrode wire may also be caused and/or exacerbated by a tendency for the wire to retract as the insertion needle is withdrawn along the wire prior to beginning of the test period. The relative movement of the needle along the wire tends to frictionally pull it in a withdrawal direction.

Also, during the test period itself, when the wire electrode is intended to remain in place, muscular motions of the patient can tend to relocate to some extent the position of the distal end of the sphenoidal electrode. This can cause detection of discharges to vary improperly over the test period.

Whatever the tendencies or reasons for improper location of the distal end of the sphenoidal wire electrode, the fact of and the extent of any such improper location are not readily discerned. Thus, when to take corrective measures during insertion procedures is often unknown.

OBJECTS OF THE INVENTION

It is an object of this invention to provide an improved apparatus and method for insertion of sphenoidal wire electrodes overcoming certain problems and shortcomings of the prior art.

Another object of this invention is to provide an apparatus and method for insertion of a sphenoidal wire electrode which will give greater reliability in detection of mesial temporal lobe epileptiform discharges.

Another object of this invention is to provide an improved apparatus and method for insertion of a sphenoidal wire electrode which more accurately and reliably places and maintains the wire distal end at the intended location.

Another object of this invention is to provide an improved apparatus and method for sphenoidal wire electrode insertion which will properly place the wire during the insertion of a insertion needle and properly maintain the wire location during withdrawal of an insertion needle.

Another object of this invention is to provide a sphenoidal wire electrode which will reliably maintain its position during the test period and yet may be withdrawn without damage or discomfort to the patient.

These and other important objects will be apparent from the descriptions of this invention which follow.

SUMMARY OF THE INVENTION

This invention is an improved apparatus and method for insertion of the sphenoidal wire electrode. The apparatus is of the type including a hollow needle having a slant-tip and an opposite grip end for holding during insertion and withdrawal of the needle and carrying the electrode a wire within the hollow needle.

In the apparatus of this invention, the wire has a turned-back distal portion which is beside the wall of the needle and substantially parallel to the needle and to the main portion of the wire, which is inside the needle. The turned-back distal portion terminates forwardly in a bend along the slant top.

The method is an improvement in the manipulation of sphenoidal wire electrodes, that is, in the steps involved in their insertion and removal. The method is of the type including the pre-test steps of inserting into the muscle and other tissue a hollow muscle and other tissue with the wire and withdrawing the needle along the wire and the post-test step of pulling the wire out of the needle.

The method of this invention includes as a first step positioning the wire along the needle with a main portion and a turned-back distal portion of the wire on opposite sides of the slant-tip proximal edge, said portions terminating forwardly in a bend in contact with the slant-tip proximal edge with one of said portions being within the needle. In the positioning step of the most preferred form of this invention, the main portion of the wire is in the needle with the turned-back distal portion positioned beside the needle and terminating forwardly along the slant-tip, just forward of the slant-tip proximal edge.

The method of this invention includes the subsequent pre-test steps of inserting the needle and positioned wire into the tissue until the slant-tip is properly located, then engaging the tissue with the turned-back portion to resist wire retraction during the withdrawal of the needle. Such engagement of the turned-back portion continues during the subsequent test period. The method also includes the post-test steps of unfolding the turned-back portion of the wire to straighten it by the initial pulling of the wire from the tissue after the test period, and then completing removal of the straightened wire.

In preferred embodiments, the wire is substantially malleable (pliable) to unfold and straighten the turned-back distal portion during the initial pulling of the wire from the tissue without damaging tissue during its removal.

In one highly preferred form, the wire is a silver, platinum or gold wire with a thin insulation adhering to it. Such metal wire is both sufficiently malleable to unfold and straighten as described above, and sufficiently conductive for proper epileptiform discharge sensing.

In highly preferred forms of this invention, the metal portion of the wire has a diameter of less than about 0.30 mm with an overall diameter of the wire, including insulation, of less than about 0.40 mm. Most preferably, the metal portion has a diameter within the range of 0.20 mm to about 0.30 mm. The insulation is removed from the turned-back distal portion to provide sufficient discharge sensing surface.

BRIEF DESCRIPTION OF THE DRAWINGS

FIG. 1 is a side elevation of a preferred sphenoidal electrode insertion apparatus of this invention.

FIG. 2 is a fragmentary enlarged primarily sectional view showing the insertable end of the apparatus.

FIG. 3 is a fragmentary side elevation of the apparatus of FIG. 1, illustrating such apparatus approaching the site of insertion. The tissue and the bone are illustrated in section.

FIG. 4 is a similar fragmentary side elevation, illustrating the apparatus fully inserted prior to withdrawal of the insertion needle.

FIG. 5 is another similar view, illustrating withdrawal of the needle to complete the pre-test steps.

FIG. 6 is another similar view showing the electrode in the position it maintains during the test.

FIGS. 7–10 are similar side elevations showing in sequence the post-test steps for electrode removal.

DETAILED DESCRIPTIONS OF PREFERRED EMBODIMENTS

The drawings illustrate a sphenoidal wire electrode insertion apparatus 20 in accordance with a preferred embodiment of this invention. Insertion apparatus 20 includes two basic parts—a hollow needle 22 and an electrode wire 24.

Needle 22 includes a straight tubular portion 26, preferably on the order of 7 cm in length, which has a slant-tip 28 at one end and an opposite grip end 30. Tubular portion 26 has a diameter and wall thickness which provide sufficient strength to eliminate any concern about needle breakage during insertion of wire electrode 24. An axial opening extends from one end to the other of needle 22, through both tubular portion 26 and grip end 30. Needle 22 by itself is similar to the needles used in sphenoidal electrode insertion in the prior art.

Wire electrode 24 includes a main wire portion 32 which extends from a proximal end beyond grip end 30 into and through all of needle 22 to slant-tip 28 thereof. Electrode 24 includes a turned-back distal portion which is itself substantially parallel and adjacent to needle 22 and parallel to maintain wire portion 32.

Turned-back distal wire portion 34 and main wire portion 32 are joined in a bend or fold 36 which is the forward termination point of both turned-back distal wire portion 34 and main wire portion 32. When ready for insertion and during insertion electrode wire 24 is positioned with respect to needle 22 such that bend 36 is at slant-tip 28. As illustrated in FIGS. 1-4, bend 36 extends closely around the proximal edge 38 of slant-tip 28 such that the distal edge 40 of slant-tip 28 is free to cut tissue during insertion without interference from wire 24.

In the insertion step, slant-tip 28 is first placed on the skin 42 at a position approximately 3–4 mm below the zygoma and 2–3 mm in front of the tragus. The proper point can be verified by asking the patient to open and close his jaw while palpating the area of proposed insertion. This should allow free palpation of the temporal mandibular joint. Needle 22 should be inserted just anterior to the temporal mandibular joint such that it does not pierce the joint capsule. Needle is preferably inserted at an angle of about 90 degrees to the surface of the skin toward the corresponding point at the opposite side of the head.

Needle 22 is inserted through muscle and other tissue 44 until slant-tip 28 strikes bone 46. This usually occurs after insertion of about 4–6 cm. At that location, wire electrode 24, including turned-back distal wire portion 24, is in a proper location for sensing of mesial temporal lobe epileptiform discharges. This position of insertion apparatus 20 is illustrated in FIG. 4.

Needle 22 is then withdrawn along wire electrode 24, as shown in FIG. 5. During and after such withdrawal, turned-back distal portion 34 of wire electrode 24 engages tissue 44. Such engagement resists unintended relocation of distal portion 34 during withdrawal of needle 22 and during the subsequent test period. After withdrawal of needle 22, a small piece of tape 48 is placed over the insertion site to help secure wire 24 in place.

During the test period, which typically lasts for extended periods of up to five days or more, engagement of turned-back distal portion 34 with tissue 44 resists any mislocation due to muscle action or the like.

After the test period, it is necessary to remove wire electrode 24. Removal includes the step of unfolding turned-back distal wire portion 34 to align it with main wire portion 32. This is accomplished by initial pulling of the wire. Thereafter, removal is completed by pulling the now-straightened wire completely from the body.

The unfolding step is facilitated by the nature of wire electrode 24. In preferred embodiments, the wire is sufficiently malleable to unfold and straighten during initial pulling of wire 24 from tissue 44 without damaging tissue during removal. As noted above, silver, platinum or gold wire having a thin layer of insulation adhering thereon is highly preferred. The insulation is removed from turned-back portion 34 and bend 36.

The metal portion of electrode wire 24 preferably has a diameter of less than about 0.30 mm and an overall diameter of, including the insulation, of less than 0.40 mm. The insulation is preferably a FEP Teflon coating less than 0.05 mm in thickness. More specifically, the metal strand preferably has a diameter within the range of 0.20 to 0.30 mm.

In one highly preferred embodiment, 30 gauge (0.25 mm diameter) silver wire which has a total diameter, including insulation, of 0.33 mm is used. In another, 32 gauge (0.20 mm diameter) silver wire which has a total diameter, including insulation, of 0.28 mm is used.

It is not necessary to remove the Teflon insulation layer at or near distal portion 34 of wire 24. The exposed wire at the tip of turned-back distal portion 34 is enough for sensing of the epileptiform discharges.

While the principles of this invention have been described in connection with specific embodiments, it should be understood clearly that these descriptions are made only by way of example and are not intended to limit the scope of the invention.

What is claimed:

1. In an apparatus for insertion of a sphenoidal wire electrode of the type having a hollow needle with a slant-tip and an opposite grip end and the wire inside the needle, the improvement comprising:

the wire having a turned-back distal portion which is beside the needle and terminates forwardly along the slant-tip;

the wire being a sole wire whereby electrical brain impulses are received in well-defined unambiguous electrical signals;

the wire having a diameter of about 0.20–0.30 mm such that it is of sufficient size for pickup of electrical brain impulses in the sphenoidal area;

the wire being of a metal selected from the class consisting of silver, platinum and gold such that despite its size it is sufficiently malleable to unfold and straighten upon an initial pulling of the wire from the tissue without damaging tissue during its removal; and the wire being free within the needle for coaxial movement with respect thereto and extending away from the distal end to beyond the grip end of the needle for electrical attachment.

2. The sphenoidal electrode insertion apparatus of claim 1 wherein the wire has an electrical insulation adhering thereto along its length except on a portion of the turned-back distal portion, the insulated wire having an overall diameter of less than about 0.40 mm.

3. In a method for manipulating a sphenoidal wire electrode of the type including the pre-test steps of inserting into the tissue a hollow needle containing the wire and withdrawing the needle along the wire and the post-test step of pulling the wire out of the tissue, the needle having a slant-tip and a grip end, the improvement comprising:

positioning the wire in the needle with a turned-back distal portion of the wire beside the needle and terminating forwardly along the slant-tip, said wire:

being a sole wire whereby electrical brain impulses are received in well-defined unambiguous electrical signals for accurate eleptogenic mapping, having a diameter of about 0.20–0.30 mm such that it is of sufficient size for pickup of electrical brain impulses in the sphenoidal area, and being free within the needle for coaxial movement with respect thereto and extending away from the distal end to beyond the grip end of the needle for electrical attachment;

inserting the needle with positioned wire into the sphenoidal tissue until the slant-tip is properly located in position near the brain;

engaging the sphenoidal tissue with the turned-back portion to resist unintended relocation during withdrawal of the needle and the subsequent test period; and unfolding the turned-back portion of the wire to straighten it by initial pulling of the wire from the tissue after the test period and then completing removal of the straightened wire, said wire being of a metal selected from the class consisting of silver, platinum and gold such that despite its size it is sufficiently malleable to unfold and straighten upon an initial pulling of the wire from the tissue without damaging tissue during its removal.

4. The sphenoidal electrode manipulation method of claim 3 wherein the wire has an electrical insulation adhering thereto along its length except on a portion of the turned-back distal portion, the insulated wire having an overall diameter of less than about 0.40 mm.

5. In a method for manipulating a sphenoidal wire electrode including the pre-test steps of inserting into the tissue a hollow needle with the wire and withdrawing the needle along the wire and the post-test step of pulling the wire out of the tissue, the needle having a grip end and an opposite slant-tip with proximal and distal edges, the improvement comprising:

positioning the wire along the needle with a main portion and a turned-back distal portion of the wire on opposite sides of the slant-tip proximal edge, said portions terminating forwardly in a bend in contact with the slant-tip proximal edge, one of said portions being within the needle, said wire:

being a sole wire whereby electrical brain impulses are received in well-defined unambiguous electrical signals for accurate eleptogenic mapping, having a diameter of about 0.20–0.30 mm such that it is of sufficient size for pickup of electrical brain impulses in the sphenoidal area, and being free within the needle for coaxial movement with respect thereto and extending away from the distal end to beyond the grip end of the needle for electrical attachment;

inserting the needle with positioned wire into the sphenoidal tissue until the slant-tip is properly located in position near the brain;

engaging the sphenoidal tissue with the turned-back portion to resist unintended relocation during withdrawal of the needle and the subsequent test period; and unfolding the turned-back portion of the wire to straighten it by initial pulling of the wire from the tissue after the test period and then completing removal of the straightened wire, said wire being of a metal selected from the class consisting of silver, platinum and gold such that despite its size it is sufficiently malleable to unfold and straighten upon an initial pulling of the wire from the tissue without damaging tissue during its removal.

6. The sphenoidal electrode manipulation method of claim 5 wherein the wire has an electrical insulation adhering thereto along its length except on a portion of the turned-back distal portion, the insulated wire having an overall diameter of less than about 0.40 mm.

* * * * *

UNITED STATES PATENT AND TRADEMARK OFFICE
CERTIFICATE OF CORRECTION

PATENT NO.  : 4,805,625

DATED       : February 21, 1989

INVENTOR(S) : Allen R. Wyler

It is certified that error appears in the above-identified patent and that said Letters Patent is hereby corrected as shown below:

Column 2, line 53, delete "needle" and insert in its place --muscle and other tissue--.

Column 5, Claim 3, line 58, change "eleptogenic" to --epileptogenic--.

Column 6, Claim 5, line 37, change "eleptogenic" to --epileptogenic--.

Signed and Sealed this

Third Day of October, 1989

Attest:

Attesting Officer

DONALD J. QUIGG

Commissioner of Patents and Trademarks